United States Patent [19]

Schwarz et al.

[11] Patent Number: 5,180,861
[45] Date of Patent: Jan. 19, 1993

[54] PROCESS FOR THE PREPARATION OF POLYCHLORO-FLUORO-CYCLO-PENTENES

[75] Inventors: Hans-Helmut Schwarz, Krefeld; Rudolf Braden, Odenthal; Albrecht Marhold, Leverkusen; Michael Negele, Cologne, all of Fed. Rep. of Germany

[73] Assignee: Bayer Aktiengesellschaft, Leverkusen, Fed. Rep. of Germany

[21] Appl. No.: 595,914

[22] Filed: Oct. 11, 1990

[30] Foreign Application Priority Data

Oct. 28, 1989 [DE] Fed. Rep. of Germany ....... 3936023

[51] Int. Cl.⁵ .............................................. C07C 17/20
[52] U.S. Cl. .................................................. 570/160
[58] Field of Search ................................ 570/160, 166

[56] References Cited

U.S. PATENT DOCUMENTS 2,449,233  12/1948  Kischitz et al.
3,149,170   9/1964  Clark et al. .......................... 570/160

FOREIGN PATENT DOCUMENTS 659436   3/1963  Canada ............................... 570/160
1900241  7/1970  Fed. Rep. of Germany ...... 570/166

*Primary Examiner*—Alan Siegel
*Attorney, Agent, or Firm*—Sprung Horn Kramer & Woods

[57] ABSTRACT

Polychloro-fluoro-cyclopentenes can be prepared by catalytic reaction of hexachlorocyclopentadiene with hydrogen fluoride in the gas phase with the addition of chlorine.

13 Claims, No Drawings

PROCESS FOR THE PREPARATION OF POLYCHLORO-FLUORO-CYCLO-PENTENES

SUMMARY OF THE INVENTION

The present invention relates to a process for the preparation of polychlorofluoro-cyclopentenes by reaction of halogen-containing cyclic compounds having a 5-membered ring with hydrogen fluoride in the gas phase over a catalyst, which is characterized in that hexachlorocyclopentadiene is employed as the starting material and the reaction is carried out with the addition of chlorine.

BACKGROUND OF THE INVENTION

The known process for preparing polychlorofluoro-cyclopentenes (PCFCP) by reaction of halogen-containing cyclic compounds having a 5-membered ring with HF in the gas phase over catalysts use, as the starting material, either octachlorocyclopentene (DE-OS) (German Published Specification) 1,543,015) or partly fluorinated chloro-fluoro-cyclopent-1-enes which are chlorinated on the double bond and have at least one fluorine atom in the molecule (U.S. Pat. No. 3,178,482; and U.S. Pat. No. 3,258,500). Catalysts which are employed for such reactions are active charcoals (U.S. Pat. No. 3,178,482), activated chromium gels (U.S. Pat. No. 3,258,500) or aluminum oxide doped with copper or cobalt (DE-OS (German Published Specification) 1,543,015). The processes mentioned allow only moderate conversions to PCFCP and start from starting substances which themselves are accessible only via multi-stage synthesis.

According to U.S. Pat. No. 2,449,233, hexachlorocyclopentadiene is converted into PCFCP in the liquid phase under pressure with $SbF_5$ produced in situ from $SbCl_5$ and $HF/Cl_2$. This process is laborious and requires large amounts of expensive Sb compounds which pollute the environment.

DE-OS (German Published Specification) 1,900,241 describes the hydrofluorination of partly and completely chlorinated olefines in the gas phase over Sb-containing supported catalysts on $Al_2O_3$, which is said to lead to the corresponding saturated fluoroalkanes. In this DE-OS (German Published Specification), hexachlorocyclopentadiene is mentioned as the cyclic halogenohydrocarbon on page 6, line 8, but a description of the reaction conditions and the products formed is absent; thus, above all no PCFCP is mentioned as a product.

It is furthermore known from DE-OS (German Published Specification) 2,057,398 that aliphatic chlorohydrocarbons can be split in the absence of catalysts with $Cl_2$ and HF at temperatures of 400° to 800° C. to give carbon tetrachloride or fluorochloromethanes. According to page 3, line 22 of this DE-OS (German Published Specification), this also applies to perchlorinated cycloaliphatics.

It was thus surprising that the present process according to the invention allows chlorine-fluorine exchange on hexachlorocyclopentadiene to form halogenated cyclopentenes of varying degrees of fluorination. This is because DE-OS (German Published Specification) 1,543,015 states on page 12, line 13, that more highly (completely) halogenated (cyclo)-aliphatics can be fluorinated more rapidly, so that this DE-OS (German Published Specification) considers the octachloro-cyclopentene which is more troublesome to prepare to be necessary, although this also produces only moderate results. The starting substance hexachlorocyclopentadiene is an industrially accessible compound which can be prepared conventionally (Ullmanns Enzyklopädie der technischen Chemie (Ullmann's Encyclopaedia of Industrial Chemistry), 5th edition, Volume A8 (1987), 231; and Chem. Rev. 58 (1958),250).

DETAILED DESCRIPTION OF THE INVENTION

For reaction, hexachloro-cyclopentadiene is introduced in the vapour state and as a mixture with HF and $Cl_2$ into a catalyst bed. The reaction can be carried out in a fixed bed or in a fluidized bed. The reaction temperature is in the range from 300° to 450° C., preferably from 320° to 420° C. The reaction is as a rule carried out under normal pressure.

7–40 mol, preferably 10–20 mol, of HF per mol of the starting material are employed for the reaction. Excess HF which leaves the reactor without being used is advantageously recycled.

The reaction is carried out in the presence of 0.1 to 2 mol of chlorine, preferably 0.3 to 1.1 mol of chlorine, per mol of the starting material.

Catalysts are employed in the process according to the invention, these also including, in addition to those mentioned above, iron, zinc salts on supports (for example active charcoal, $Al_2O_3$ or $AlF_3$), $Al_2O_3$ doped with metal salts, bismuth-containing catalysts, oxides and other lanthanide compounds on catalyst supports. The reaction is preferably carried out over a catalyst in which the essential active compound is a compound of bismuth, a lanthanice or chromium. Catalysts containing bismuth or a lanthanide are particularly preferred.

Such particularly preferred bismuth catalysts include those containing compounds of the alkaline earth metals, which contain 0.005–0.8 gA of bismuth, preferably 0.008–0.7 gA of bismuth, per mol of the support compound and may furthermore contain promoters and/or inert additives (for example graphite). An essential component of these catalysts are alkaline earth metal compounds which originate from at least one compound from the group comprising carbonates, hydroxides, oxides and fluorides of the alkaline earth metals, preferably those which originate from at least one compound from the group comprising magnesium oxide, calcium oxide and barium oxide. Such bismuth catalysts can furthermore contain, as promoters, at least one compound of elements of sub-group VII and VIII of the periodic table of the elements (Mendeleev) or of the lanthanides; the gram atom ratio of the promoter elements to the element bismuth in this case is 0.01–200:1, preferably 0.1–10:1. Inert additives, for example graphite, can be added to the catalysts. Such catalysts are preferably free from inert additives.

These catalysts can be prepared by known processes, for example merely by making a paste of the active compounds with as little water as possible and intimately mixing the pasty mass thus obtained. Granules, for example, can be prepared from such a paste and dried. In the dried state, a catalyst prepared in this manner is advantageously treated with excess hydrogen fluoride at a temperature of 20°–500° C., preferably 100°–500° C. and particularly preferably 120°–420° C. Heat treatment at 200°–400° C., preferably 300°–375° C., can be included between the drying operation and the treatment operation with hydrogen fluoride.

Particularly preferred catalysts based on lanthanides as active compounds include those from at least one oxidic compound of lanthanides or of compounds of the lanthanides on catalyst supports. Preferred lanthanides are cerium, lanthanum and dysprosium. The catalyst support can be, for example, $Al_2O_3$, $AlF_3$, active charcoal, coke, $CaF_2$ or $ZnF_2$. Such catalysts are also prepared by known methods, for example by mixing the starting substances to a paste as described above, and after drying are preferably treated with excess hydrogen fluoride at a temperature of 20°–500° C., preferably 100°–500° C., particularly preferably 120°–420° C. Heat treatment at 200°–400° C., preferably 300°–375° C., can also be included between the operations of drying and treatment with hydrogen fluoride in the case of this group of catalysts. The lanthanide compounds make up 0.1–100% by weight of the total weight of the catalyst, weight contents of less than 100% applying to the case where catalyst supports are also used. In this case where catalyst supports are also used, the weight of the lanthanide compounds is preferably 2–30% by weight of the total weight of the catalyst.

Polychloro-fluoro-cyclopentenes are of industrial importance as intermediate products for plastics precursors.

EXAMPLE 1

2.5 parts by weight of $Bi(NO_3)_3.5 H_2O$ and 1.2 parts of 65% strength nitric acid were dissolved in 3.6 parts of water. 1 part of $Fe(NO_3)_3.9 H_2O$ was added. This solution was added to 1.5 parts by weight of magnesium oxide and the pasty mass thereby formed was intimately kneaded. The pasty reaction product was then granulated and the granules were dried at 100° C. for 16 hours. Thereafter, the catalyst was heated at 400° C. for 6 hours. The atomic ratio of Mg:Bi:Fe was 1:1.29:0.17.

0.33 l of the contact substance was treated with 5 mol of hydrogen fluoride (HF) at 350° C. in a tube of 5 cm internal diameter and 100 cm length. The duration of the HF treatment was about 3 hours. In this treatment, HF was diluted with $N_2$ in a molar ratio of 1:2.

102 g of hexachlorocyclopentadiene, 210 g of HF and 9.5 g of chlorine were passed over 200 ml of this catalyst at 350° C. in the course of 5 hours. The reaction gases were condensed in an ice/water mixture. 72.4 g of an organic phase which, according to analysis by gas chromatography (GC) contained 58.4% of 1,2-dichloro-3,3,4,4,5,5-hexafluorocyclopent-1-ene, 29.1% of trichlorinated cyclopentenes (1,2,4-trichloro-3,3,4,5,5-pentafluorocyclopent-1-ene and isomers with 1,2-chlorination) and 8.1% of tetrachlorinated cyclopentenes (1,2,4,4-tetrachloro-3,3,5,5-tetrafluorocyclopent-1-ene and isomers with 1,2-chlorination), separated out. The hexachlorocyclopentadiene had reacted completely.

EXAMPLE 2

According to Example 1, a catalyst was prepared from 162.8 g of $Ce(NO_3)_3.6 H_2O$, 255 g of water and 500 ml of aluminium oxide SAS 350 (Rhone-Poulenc) and was activated.

100 g of hexachlorocyclopentadiene, 200 g of HF and 9 g of chlorine were passed over 120 ml of this catalyst at 410° C. in the course of 5 hours.

On absorption of the reaction gases in ice-water, 87.5 g of an organic phase which contained 2.1% of 1,2-dichloro-3,3,4,4,5,5-hexafluorocyclopent-1-ene, 23.8% of 1,2,4-trichloro-3,3,4,4,5,5-pentafluorocyclopent-1-ene (and isomers as in Example 1), 35.1% of 1,2,4,4-tetrachloro3,3,5,5-tetrafluorocyclopent-1-ene (and isomers as in Example 1) and 3% of hexachlorocyclopentadiene were formed.

EXAMPLE 3

1,000 ml of $Al_2O_3$ of type SAS 350 (Rhone-Poulenc) in the form of 3–6 mm beads were impregnated with an aqueous solution which contained 2.1 mol of chromium-(III) chloride. The catalyst beads were dried and treated with a vaporous $NH_3/H_2O$ mixture at 200°–250° C. For this, 4 mol of $NH_3$ in the form of a 30% strength aqueous solution were vaporized and passed over the catalyst in the course of 4 hours.

200 g of HF were passed over 140 ml of this catalyst at 360° C. in the course of 6 hours. 102 g of hexachlorocyclopentadiene, 170 g of HF and 23 g of chlorine were then passed over at 350° C. in the course of 5 hours. The reaction gases were condensed in ice-water. 85.4 g of an organic phase which contained 60.5% of 1,2-dichloro-3,3,4,4,5,5-pentafluorocyclopent-1-ene, 23.5% of 1,2,4-trichloro-3,3,4,5,5-pentafluorocyclopent-1-ene (and isomers as in Example 1) and 9.7% of 1,2,4,4-tetrachloro-3,3,5,5-tetrafluorocyclopent-1-ene (and isomers as in Example 1) were formed. The hexachlorocyclopentadiene content in the reaction product was 0.1%.

EXAMPLE 4

20 g of $BiCl_3$ were dissolved in 30 g of 18% strength hydrochloric acid, and 16.76 g of $FeCl_3.6 H_2O$ were dissolved in 150 g of water. The two solutions were combined and gradually kneaded intensively with 250 g of magnesium oxide, a further 170 ml of water being added. The material was dried at 100° C. in vacuo and comminuted and the fraction of particle size 2–5 mm was sieved out. This catalyst was activated by treatment with HF at 350° C. for 5 hours.

102 g of hexachlorocyclopentadiene and 201.5 g of HF were passed over 220 ml of the catalyst at 415° C. in the course of 5 hours. On condensation of the reaction gases in cold water, 68.9 g of an organic phase which contained 8.5% of 1,2-dichloro-3,3,4,4,5,5-hexafluorocyclopent-1-ene, 16.3% of 1,2,4-trichloro-3,3,4,5,5-pentafluorocyclopent-1-ene (and isomers as in Example 1), 23.8% of tetrachloro-tetrafluoro-cyclopentenes, 18.4% of pentachloro-trifluoro-cyclopentenes, 13.3% of mono- and difluoro-polychloro-cyclopentenes and 9.7% of hexachlorocyclopentadiene were formed.

EXAMPLE 5

81.6 g of hexachlorocyclopentadiene, 108 g of HF and 10.8 g of chlorine were passed over 220 ml of the catalyst according to Example 4 at 415° C. in the course of 4 hours. On condensation of the reaction gases in water, 73.6 g of an organic phase which contained 3.8% of 1,2-dichloro-3,3,4,4,5,5-hexafluorocyclopent-1-ene, 15.6% of 1,2,4-trichloro-3,3,4,5,5-pentafluorocyclopent-1-ene (and isomers as in Example 1), 33.7% of 1,2,4,4-tetrachloro3,3,5,5-tetrafluorocyclopent-1-ene (and isomers as in Example 1), 17.0% of pentachloro-trifluorocyclopent-1ene, 13% of di- and monofluorochlorocyclopent-1-ene and 6.6% of hexachlorocyclopentadiene were formed.

What is claimed is:

1. A process for the preparation of polychloro-fluorocyclopentenes having from 4 to 6 fluoro atoms by reaction of halogen-containing cyclic compounds having a 5-membered ring with hydrogen fluoride in the gas phase over a catalyst selected from the group consisting of catalysts wherein the essential active compound is a bismuth, lanthanide, or chromium containing compound, wherein hexachlorocyclopentadiene is employed as a starting material, hydrogen fluoride is present in an amount from about 7-40 mol per mol of halogen-containing cyclic compound, the reaction is carried out in the presence of from about 0.1-2 mol of $Cl_2$ per mol of starting material, and at a temperature in the range of from 300° to 450° C.

2. The process of claim 1, which is carried out in the temperature range of from 320° to 410° C.

3. The process of claim 1, wherein 10-20 mol of hydrogen fluoride are employed per mol of the starting material.

4. The process of claim 1, wherein the reaction is carried out in the presence of 0.3-1.1 mol of chlorine.

5. The proces of claim 1, wherein the catalyst contains bismuth or a lanthanide.

6. The process of claim 5, wherein that bismuth is employed in combination with an alkaline earth metal compound.

7. The process of claim 6, wherein iron, cerium, lanthanum or dysprosium is added to the bismuth/alkaline earth metal catalyst as a promoter.

8. The process of claim 5, wherein the lanthanide is applied to a support which consists of at least one compound from the group comprising $Al_2O_3$, $AlF_3$, active charcoal, coke, $CaF_2$ or $ZnF_2$.

9. The process of claim 6, wherein 0.005-0.8 gA of bismuth are present per mol of the support compound.

10. The process of claim 9, wherein 0.008-0.7 gA of bismuth are present per mol of the support compound.

11. The process of claim 7, wherein the gram atom ratio of the promoter elements to the element bismuth is 0.01-200:1.

12. The process of claim 11, wherein the gram atom ratio of the promoter elements to the element bismuth is 0.1-10:1.

13. The process of claim 5, wherein the catalyst is treated in the dry state with excess hydrogen fluoride at a temperature of 20°-500° C. it being possible that a heat treatment at 200°-400° C. can be included between the drying operation and the treatment operation with hydrogen fluoride.

* * * * *